US009028487B2

United States Patent
McLawhorn et al.

(10) Patent No.: US 9,028,487 B2
(45) Date of Patent: May 12, 2015

(54) EXPANDABLE PROBE

(75) Inventors: Tyler E. McLawhorn, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 284 days.

(21) Appl. No.: 13/526,906

(22) Filed: Jun. 19, 2012

(65) Prior Publication Data

US 2012/0330297 A1  Dec. 27, 2012

Related U.S. Application Data (60) Provisional application No. 61/499,270, filed on Jun. 21, 2011.

(51) Int. Cl.
| | | |
|---|---|---|
| A61B 18/18 | (2006.01) | |
| A61B 18/14 | (2006.01) | |
| A61B 18/20 | (2006.01) | |
| A61B 17/00 | (2006.01) | |
| A61B 18/00 | (2006.01) | |

(52) U.S. Cl.
CPC ......... *A61B 18/1445* (2013.01); *A61B 18/1815* (2013.01); *A61B 18/20* (2013.01); *A61B 2017/00867* (2013.01); *A61B 2018/00488* (2013.01); *A61B 2018/00577* (2013.01); *A61B 2018/1472* (2013.01); *A61B 2217/007* (2013.01)

(58) Field of Classification Search
CPC ...... A61B 18/00; A61B 18/04; A61B 18/082; A61B 18/14; A61B 18/18

USPC ........................................................... 606/41
See application file for complete search history.

(56) References Cited

U.S. PATENT DOCUMENTS

| | | | | |
|---|---|---|---|---|
| 6,068,629 | A  * | 5/2000 | Haissaguerre et al. | 606/41 |
| 6,574,492 | B1 * | 6/2003 | Ben-Haim et al. | 600/374 |
| 7,507,238 | B2   | 3/2009 | Edwards et al. | |

(Continued)

FOREIGN PATENT DOCUMENTS

| | | |
|---|---|---|
| EP | 1 849 424 A1 | 10/2007 |
| JP | 2010-183927 A | 8/2010 |
| WO | WO 2006/055166 A2 | 5/2006 |
| WO | WO 2009/032623 A2 | 3/2009 |

OTHER PUBLICATIONS

International Search Report mailed Sep. 11, 2012 for International Application No. PCT/US2012/043061.

(Continued)

*Primary Examiner* — Robert N Wieland
(74) *Attorney, Agent, or Firm* — Brinks Gilson & Lione (57) ABSTRACT

An expandable probe and a method of delivering energy to a tissue using the expandable probe are provided. The expandable probe includes an elongate shaft having a proximal portion, a distal portion, a lumen extending at least partially therethrough and a longitudinal axis. The expandable probe also includes an arm operably connected to the distal portion. The arm has a first surface including an electrode extending over at least a portion of the first surface and the electrode is operably connectable to an energy source. The arm has a closed configuration and an expanded configuration where the arm in the closed configuration extends substantially parallel to the longitudinal axis and in the expanded configuration the arm extends away from the longitudinal axis.

20 Claims, 10 Drawing Sheets

(56) References Cited

U.S. PATENT DOCUMENTS

| | | |
|---|---|---|
| 2003/0181900 A1* | 9/2003 | Long .............................. 606/41 |
| 2004/0215296 A1 | 10/2004 | Ganz |
| 2011/0106074 A1* | 5/2011 | Kunis et al. ..................... 606/41 |

OTHER PUBLICATIONS

Written Opinion mailed Sep. 11, 2012 for International Application No. PCT/US2012/043061.

* cited by examiner

EXPANDABLE PROBE

RELATED APPLICATIONS

This application claims the benefit of U.S. Provisional Application No. 61/499,270, filed Jun. 21, 2011, which is incorporated by reference herein in its entirety.

BACKGROUND

Millions of people suffer from progressive gastroesophageal reflux disease (GERD) which is characterized by frequent episodes of heartburn, typically on at least a daily basis. Without adequate treatment, GERD can cause erosion of the esophageal lining as the lower esophageal sphincter (LES), a segment of smooth muscle located at the junction of the stomach and the esophagus, gradually loses its ability to function as the barrier that prevents stomach acid reflux. Chronic GERD can also cause metaplasia to the inner lining of the esophagus where the normal squamous mucosa changes to columnar mucosa, also known as Barrett's esophagus. Barrett's esophagus can progress to esophageal cancer if left untreated.

Endoscopic treatment of Barrett's esophagus includes endoscopic mucosal resection (EMR). One method of performing EMR involves ablation of the mucosal surface by heating the surface until the surface layer is no longer viable. The dead tissue is then removed.

Treatment devices for performing EMR have been developed using bipolar ablation technology that includes extending a distal end of a probe to the target tissue and delivering energy to the tissue by either touching the distal end of the probe or the side of the probe against the tissue and supplying energy to the probe to ablate the tissue in contact with the probe. The probes may be provided on an inflatable balloon. The balloon must be inflated to a predetermined size to achieve contact with the diseased tissue for delivery of the appropriate amount of energy from the bipolar ablation device to ablate the diseased tissue. In order to determine the correct size and balloon pressure to achieve adequate ablation, a sizing balloon must first be introduced into the esophagus. The sizing balloon adds an extra step to the procedure when a balloon inflated probe is used for tissue ablation. In addition, the inflated balloon is positioned in front of the endoscope viewing window, preventing direct visualization of the target tissue and potentially leading to ablation of healthy tissue or incomplete ablation of diseased tissue.

Another potential drawback of the current ablation probes is that the size is limited in that the contact area available for one energy application is limited by the size of the accessory channel of the endoscope. Most of the current ablation probes have an outer diameter of either 7 French (Fr) or 10 Fr. In many patients, the area of the tissue needing treatment is larger than the size of the probe and multiple repositionings and applications of energy to the probe are needed to adequately ablate the diseased tissue.

What is needed in the art is an ablation treatment device that is simple to use, that minimizes the number of steps and time required for a treatment procedure, that is sized to fit in a standard accessory channel and then expand once the distal end of the device exits the accessory channel and that provides treatment under direct endoscopic visualization.

BRIEF SUMMARY

Accordingly, it is an object of the present invention to provide a device and a method having features that resolve or improve on one or more of the above-described drawbacks.

In one aspect, an expandable probe is provided. The expandable probe includes an elongate shaft having a proximal portion, a distal portion, a lumen extending at least partially therethrough and a longitudinal axis. The expandable probe also includes an arm operably connected to the distal portion. The arm has a first surface including an electrode extending over at least a portion of the first surface and the electrode is operably connectable to an energy source. The arm has a closed configuration and an expanded configuration where the arm in the closed configuration extends substantially parallel to the longitudinal axis and in the expanded configuration the arm extends away from the longitudinal axis.

In another aspect, a method of delivering energy to a tissue site within a patient's lumen is provided. The method includes positioning an expandable probe within a patient's lumen. The expandable probe includes an elongate shaft having a proximal portion, a distal portion, a lumen extending at least partially therethrough and a longitudinal axis. The expandable probe also includes an arm operably connected to the distal portion, the arm having a first surface including an electrode extending over at least a portion of the first surface. The method further includes supplying energy to the electrode and ablating the tissue.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the expandable probe to a patient. Hence the term "distal" means the portion of the expandable probe that is farthest from the physician and the term "proximal" means the portion of the expandable probe that is nearest to the physician.

Figures 1, 2:
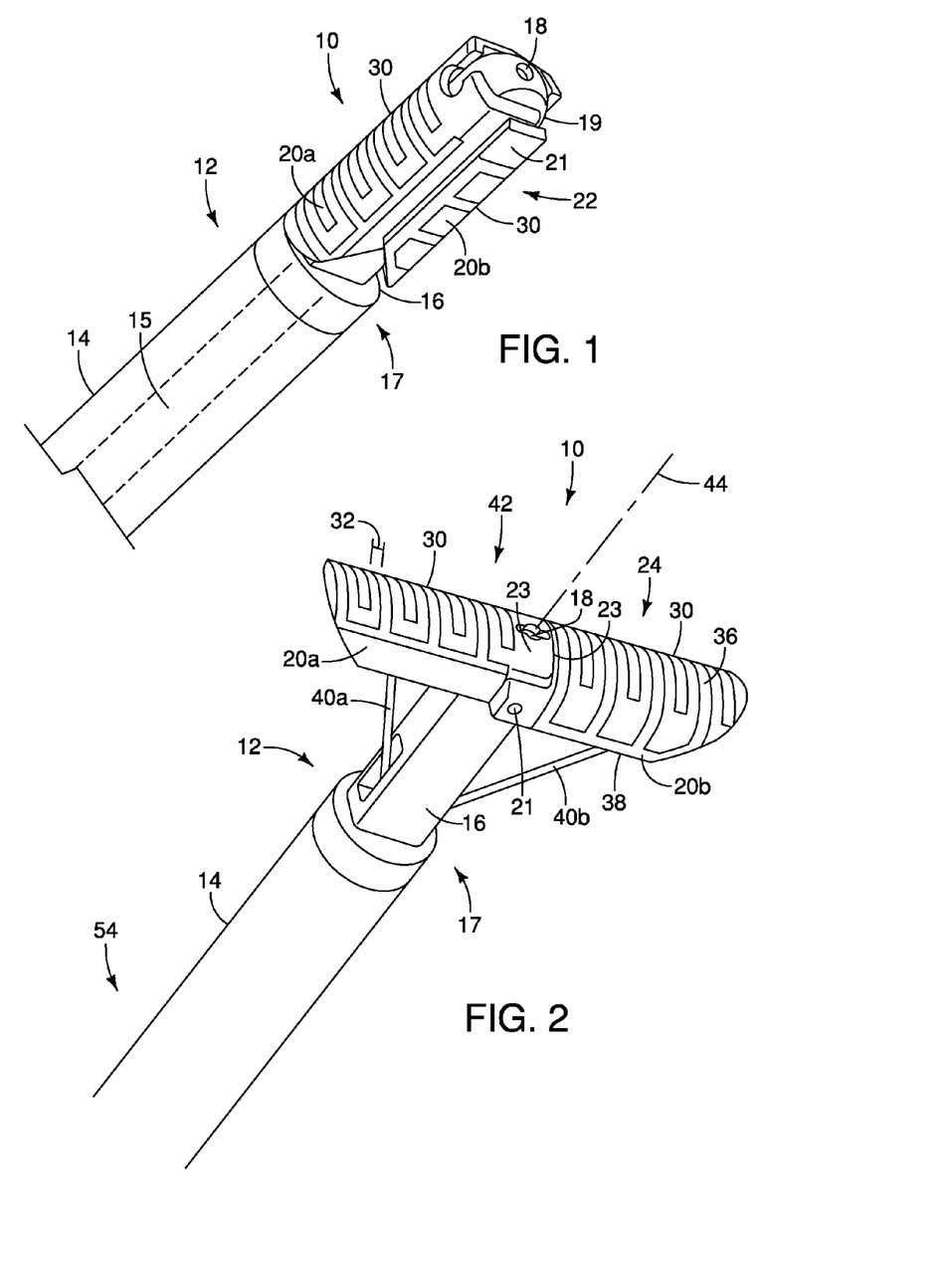
FIG. 1 is a perspective view of an expandable probe in a closed configuration in accordance with an embodiment of the present invention.
FIG. 2 is a perspective view of the expandable probe shown in FIG. 1 in an expanded configuration.

FIGS. 1 and 2 illustrate an embodiment of an expandable probe 10 in accordance with the present invention. The expandable probe 10 is operably connected to a distal portion 12 of an elongate shaft 14. The expandable probe 10 may be mounted to a tip portion 16 at the distal end 17 of the elongate shaft 14. One or more lumens 15 may extend through at least a portion of the elongate shaft 14. A port 18 may be connected to the lumen 15 and positioned at a distal end 19 of the tip portion 16. The port 18 may also be positioned proximal to the distal end 19. The port 18 may be provided for fluid delivery to the treatment site. The distal tip portion 16 may be integral with the shaft 14 or may be provided separately from the shaft 14 and connected thereto. The expandable probe 10 may include arms 20 operably connected to the tip portion 16. The arms 20 are movable between a closed configuration 22 (shown in FIG. 1) and an expanded configuration 24 (shown in FIG. 2). A pair of arms 20a and 20b is illustrated in FIGS. 1 and 2, however, the expandable probe 10 may also include one, three or more arms 20 and is not limited to two arms 20. The arms 20 may be movable about a pivot 21, although other attachments for the arms 20 are also possible. The arms 20 include a first side 36 and a second side 38 (see FIG. 7). Each of the arms 20 includes one or more electrodes 30 that may be provided on the first side 36, the second side 38, or both, as described in more detail below.

The arms 20 may be expanded from the closed configuration 22 where the arms 20 are substantially parallel to the elongate shaft 14 to the expanded configuration 24 where the arms 20 extend away from the elongate shaft 14. The arms may be expanded using any method known to one skilled in the art. For example, the arms 20 may be expanded by mechanical, pneumatic, electrical, shape memory and the like. By way of non-limiting example, the arms 10 may be expanded using wires 40 operably connected to the arms 20. As shown in FIG. 2, the wires 40 may be extended distally to expand the arms 20 where a wire 40a pushes the arm 20a distally and a wire 40b pushes the arm 20b distally. The arms 20a, 20b may be controlled together or separately. In some embodiments, the arms 20a and 20b may be pushed into the expanded configuration 24 so that the first sides 36 of arms 20a, 20b form a substantially planar surface 42 that extends substantially perpendicular to a longitudinal axis 44 of the elongate shaft 14. As shown, each arm 20a, 20b extends at about a 90° angle from the longitudinal axis 44. The first sides 36 can be positioned adjacent to the tissue to be treated. The arms 20a, 20b may also be controlled separately so that one arm 20a may be distally extended by the wire 40a while the other arm 20b remains positioned against the shaft 14 (discussed in more detail below). In addition, the arms 20 may be extended to any angle between about 0° and 180° relative to the longitudinal axis 44. The arms 20 may be returned to the closed configuration 22 by pulling proximally on the wires 40. The wires 40 may be moved and locked in position by a handle 50 shown in FIG. 4 and discussed below. In some embodiments, the wires 40 may be connected to the second side 38 of the arms 20 as shown in FIG. 2. Alternatively, the wires 40 may move the arms 20 to the expanded configuration 24 by pulling the wires 40 in a proximal direction and to the closed configuration 22 by pushing the wires 40 in a distal direction. For example, the wires 40 may be connected to an end portion 23 of each arm 20 that is operably connected to the distal portion 16 of the shaft 14 so that the wires 40 may be pulled proximally to expand the arms 20 to the expanded configuration 24. The wires 40 connected to the end portions 23 may be pushed distally to move the arms 20 to the closed configuration 22 shown in FIG. 1. (Not shown.)

Figure 3:
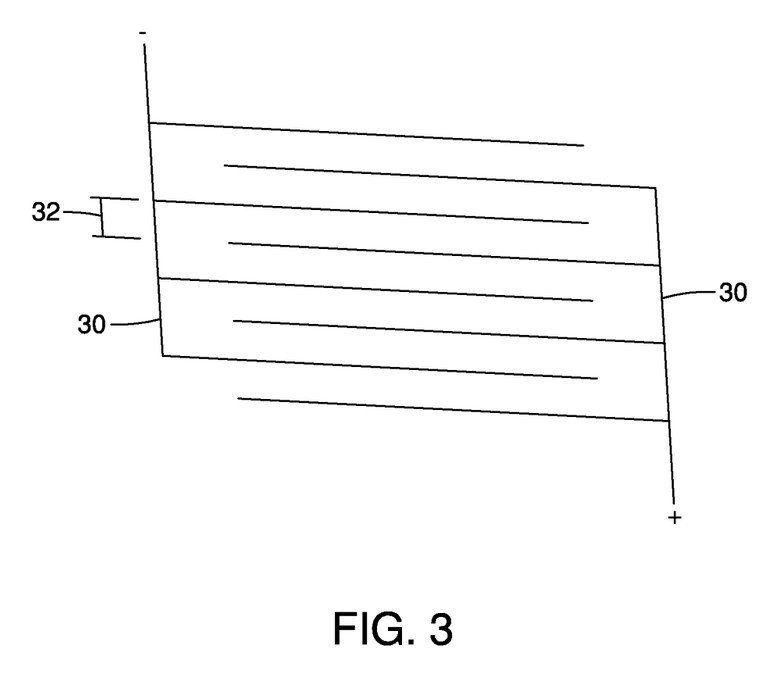
FIG. 3 is a partial view of electrodes in accordance with an embodiment of the present invention.

As discussed above, each of the arms 20 may include at least one electrode 30. The electrodes 30 may be provided in pairs to form a bipolar delivery device. One electrode 30 of the pair is a positive electrode and other electrode 30 of the pair is a negative electrode. The positive and negative electrodes 30 alternate in the pattern as shown in FIG. 3. Distance 32 between the electrodes 30 may be optimized to control the depth of ablation of the target tissue. The distance 32 between positive and negative electrodes 30 may be between about 0.025 mm and about 5 mm, but is not limited to these distances. Other spacing distances between electrodes and electrode patterns are also possible and depend on the target tissue, the depth of the lesion, the type of energy, the length of application of the energy to the tissue and the like. In some embodiments, one or more electrodes 30 may be provided as a monopolar delivery device and may include a grounding pad or an impedance circuit (not shown). In some embodiments, the electrodes 30 may cover the entire arm 20 or a portion of the arm or be selectively energizable so that only the portion of the arms 20 contacting the tissue to be treated is activated. For example, the electrodes 30 operably connected to arms 20a and 20b may be independently activated.

Figure 4:
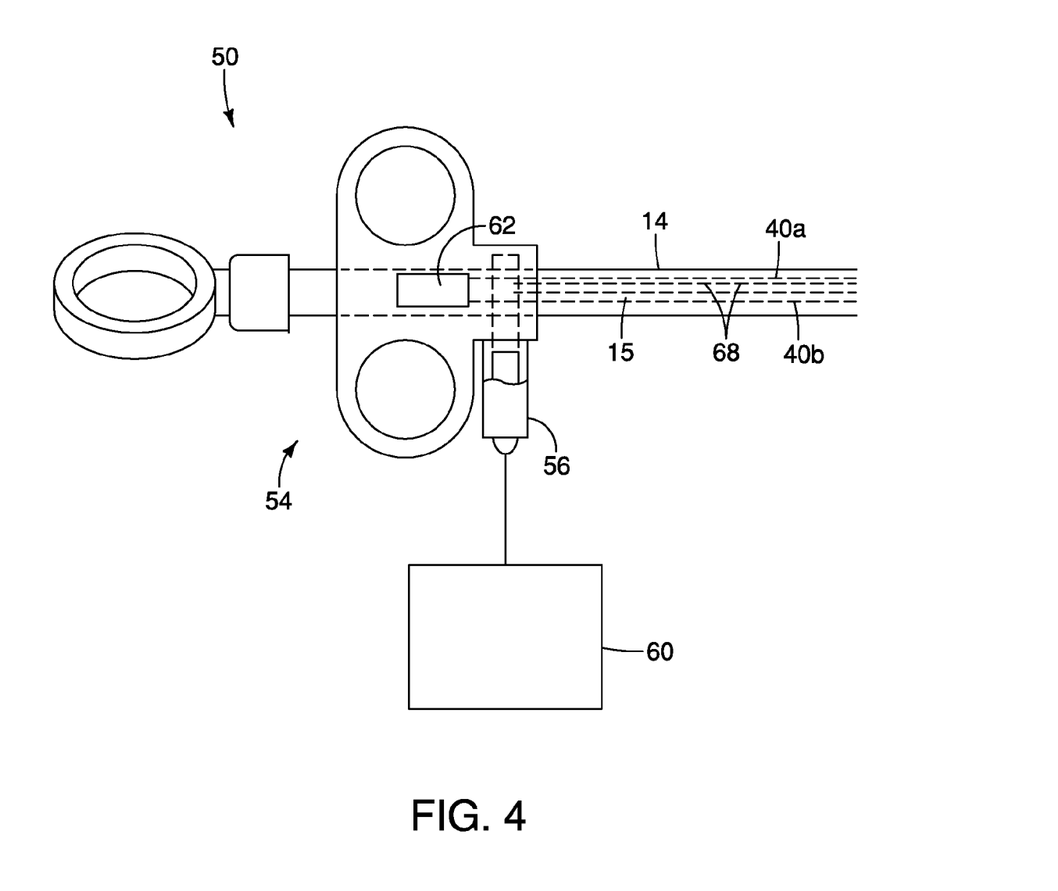
FIG. 4 is a partial side view of a handle of an expandable probe.

As shown in FIG. 4, the handle 50 is provided at a proximal portion 54 of the expandable probe 10. The handle 50 may be any type of handle that is operable to control the movement of the arms 20 of the expandable probe 10. The handle 50 is operable to control movement of the arms 20 between the expanded configuration 24 and the closed configuration 22, for example by movement of the wires 40 proximally and distally. The handle 50 may include a connector 56 for operably connecting the electrodes 30 to an energy source 60. In some embodiments, the energy source 60 may be a radio frequency source. However, other types of energy sources 60 may also be used to provide energy to the expandable probe 10. By way of non-limiting example, additional possible energy sources may include microwave, ultraviolet and laser energies. The electrodes 30 may be connected to the power source 60 by an electrical conductor, such as one or more wires 40 that are used to move the arms 20. These electrically conducting wires 40 may be insulated so that the energy is delivered to the electrodes 30 only. In some embodiments, separate electrically conducting wires 68 may be provided that extend from the electrodes 30 to the connector 56 that connects to the energy source 60. The wires 68 may extend through the lumen 15 of the shaft 14 as shown in FIG. 4. Alternatively, the wires 68 may extend external to the shaft 14 and may optionally include a sleeve surrounding the shaft 14 and the wires 68 (not shown). The handle 50 may include a lock 62 shown in FIG. 4 to releasably lock the arms 20 of the expandable probe 10 in position for delivery of energy to the treatment site. The lock 62 may releasably lock the wires 40 at any proximal/distal positioning of the arms 20 so that the expandable probe 10 may be locked in any position relative to the longitudinal axis 44 that is suitable for treating the tissue.

Figure 5:
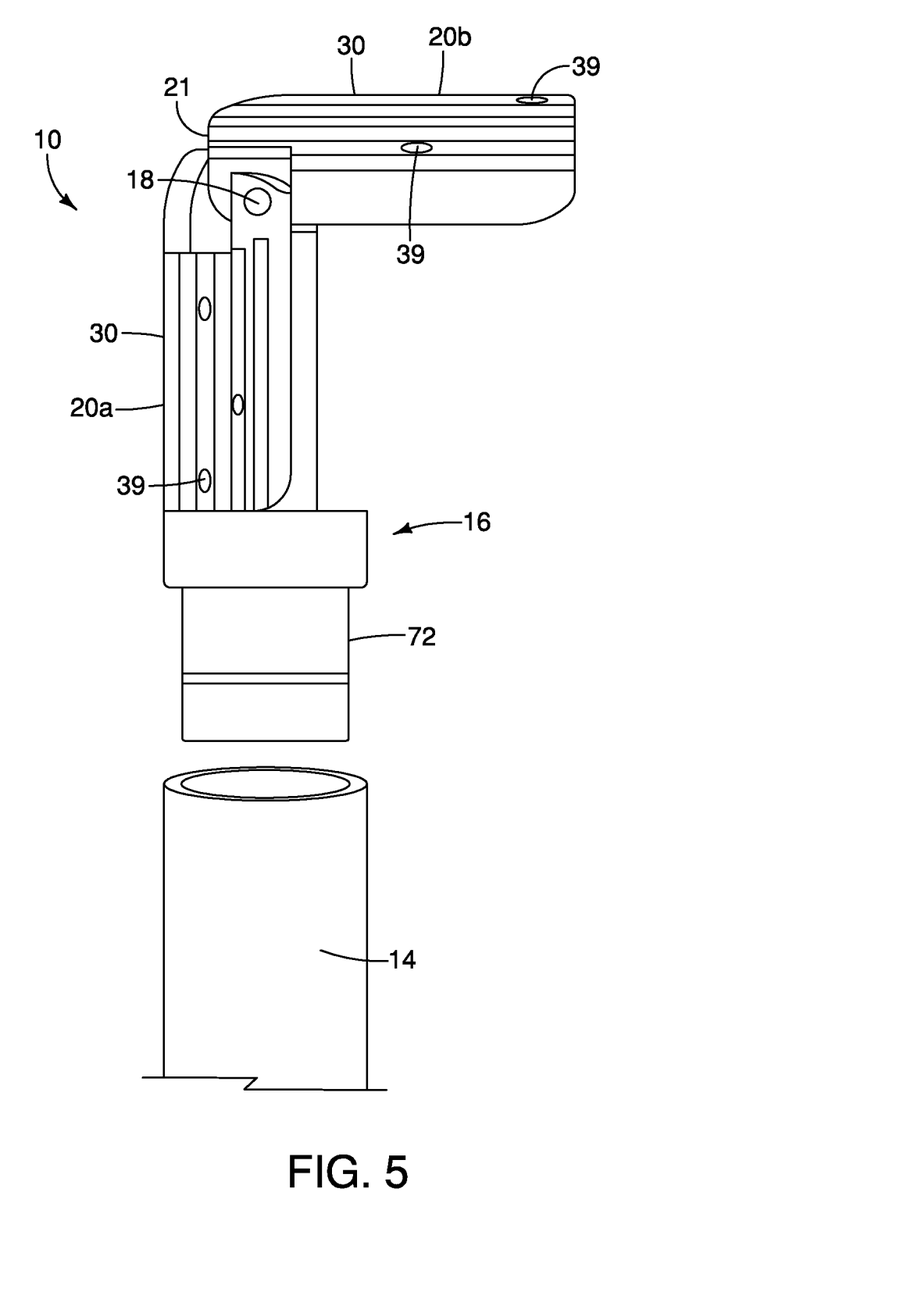
FIG. 5 is a side view of the embodiment of an expandable probe.

FIG. 5 illustrates an embodiment of the expandable probe 10 having one arm 20b expanded and another arm 20a closed. The arms 20a, 20b may be expanded and closed as discussed above. Each arm 20a and 20b includes electrodes 30 that may be energized to treat an area of tissue. The electrodes 30 may be energized on both the expanded configuration 24 and the closed configuration 22. As shown in FIG. 5, the electrodes 30 are in a generally longitudinal pattern extending along each arm 20. Additional patterns of electrodes may also be used including, but not limited to circular, rectangular, generally axially extending, angled with respect to the arms, and the like. Bipolar electrodes 30 may be alternating as shown in FIG. 3. The electrodes 30 on the arms 20a and 20 may be energized separately or together, and portions of the electrodes 30 on each arm 20 may be separately energized as will be understood by one skilled in the art.

FIG. 5 also illustrates a plurality of flush ports 39 positioned between the electrodes 30 on the arms 20. Depending on the spacing of the electrodes 30, the ports 39 may be provided on the arms 20 in addition to or as an alternative to the port 18 provided at the distal end 19 (shown in FIG. 1). The ports 39 may be operably connected to the lumen 15 through the arms 20 to provide fluid delivery to the ports 39. Alternative fluid delivery configurations may also be provided with the expandable probe 10. As shown in FIG. 5, the distal portion 16 may be formed separately from the shaft 14 and connected thereto. A proximal end portion 72 of the distal portion 16 may be sized to fit in the distal end 17 of the shaft 14 and mounted therein. The distal portion 16 may also be integrally formed with the shaft 14.

In some embodiments, the electrodes 30 are provided over a material forming the arms 20 as shown in FIGS. 1 and 2, for example. The material forming the arms 20 in some embodiments is made primarily of a substantially transparent or translucent polymer such as polytetrafluorothylene (PTFE) for facilitating viewing of the treatment site from the viewing port of an endoscope. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon. By way of non-limiting example, the electrodes may be secured to the arms using an adhesive backing, taping, gluing crimping, welding and the like.

Figure 6:
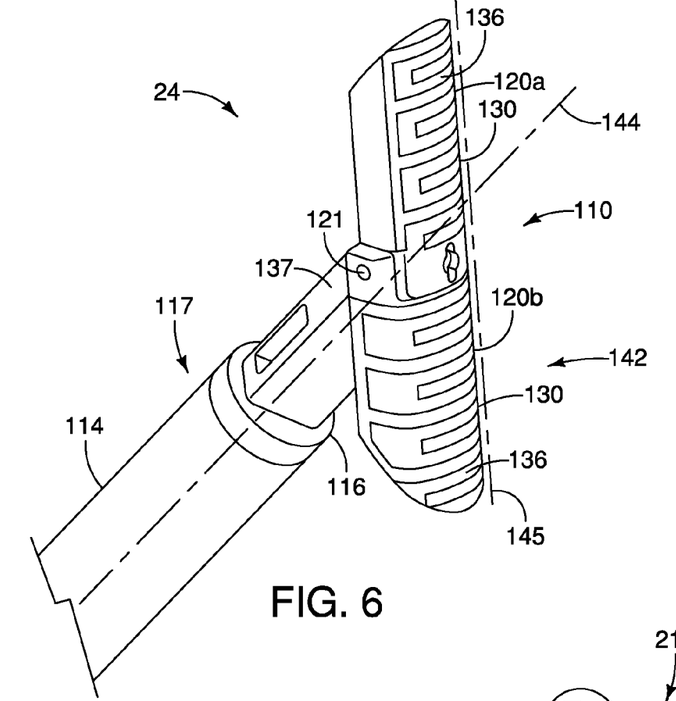
FIG. 6 is a perspective view of an embodiment of an expandable probe including a hinge member.

An embodiment of an expandable probe 110 is shown in FIG. 6. The expandable probe 110 is similar to the expandable probe 10 described above and includes arms 120a, 120b and electrodes 130 operably connected to the arms 120. The arms 120a, 120b are pivotally connected at a pivot 121 to a distal portion 116 connected to a shaft 114. The pivot 121 allows the arms 120a, 120b to move between the closed configuration 22 (see FIG. 1) and the expanded configuration 24. The expandable probe 110 further includes a hinge member 137 to allow arms 120a, 120b to pivot relative to the distal portion 116 to provide additional angles for the arms 120a, 120b to contact the tissue at the treatment site. The hinge member 137 allows the probe 110 to swivel in any angle so the physician can approach the target tissue at any angle appropriate for treatment. As shown in FIG. 6, by way of non-limiting example, the arms 120a, 120b are both extended away from the distal portion 116 in the expanded configuration 24 with first sides 136 forming a planar surface 142. An axis 145 extending along the planar surface 142 intersects a longitudinal axis 144 at other than a 90° angle when the arms 120a, 120b are pivoted on the hinge member 137. The arms 120a, 120b may also be extended at different angles relative to each other.

Figure 7:
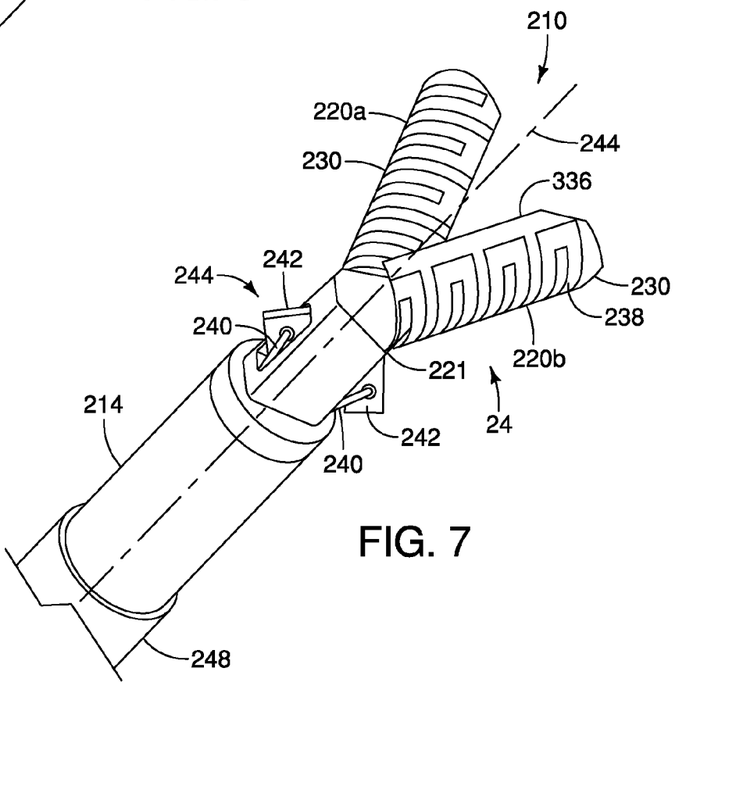
FIG. 7 is a perspective view of an alternative embodiment of an expandable probe in accordance with the present invention.
Figure 8:
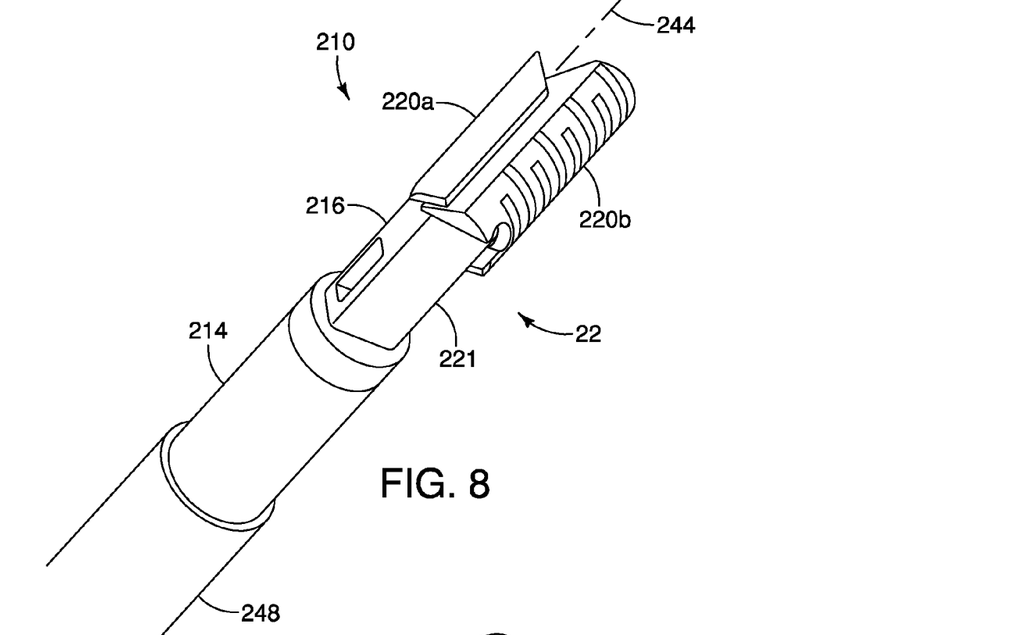
FIG. 8 is a perspective view of the embodiment shown in FIG. 7 in the closed configuration.

FIGS. 7 and 8 illustrate an embodiment of an expandable probe 210. The probe 210 includes arms 220a, 220b that are movable between the closed configuration 22 (FIG. 8) and the expanded configuration 24 (FIG. 7). The arms may be expanded using any mechanism discussed above. By way of non-limiting example, the arms 220a, 220b may each include a tang 242 on a proximal end 244 of the arms 220a, 220b. A wire 240 may be operably connected to the tangs 242 to move the arms between the closed configuration and the expanded configuration. The wires 240 may be moved distally to expand the tangs 242 outward from the distal portion 216 and the arms 220a, 22b away from being positioned substantially parallel to a longitudinal axis 244 as shown in FIG. 7. The arms 220a, 220b pivot about a pivot 221 to open and close. The arms 220a, 220b may be moved to the closed configuration 22 by pulling the wires 240 proximally and moving the tangs 242 inward in to the distal portion 216 so that the arms 220a, 220b extend distally and close together as shown in FIG. 8. An outer sheath 248 may also be provided to cover the arms 220a, 220b for delivery of the expandable probe to the target tissue site. A hinge 237 may also be provided to angle the arms 220a, 220b relative to the longitudinal axis 244 as described above.

The arms 220a, 220b include electrodes 230 that may be provided on a first side 236 and a second side 238. The arms 220a, 220b may be formed of flexible material so that the arms 220a, 220b flex and the electrodes 230 contact the tissue on either the first side 236 or the second side 238 depending on the side that is exposed toward the tissue.

Figure 9:
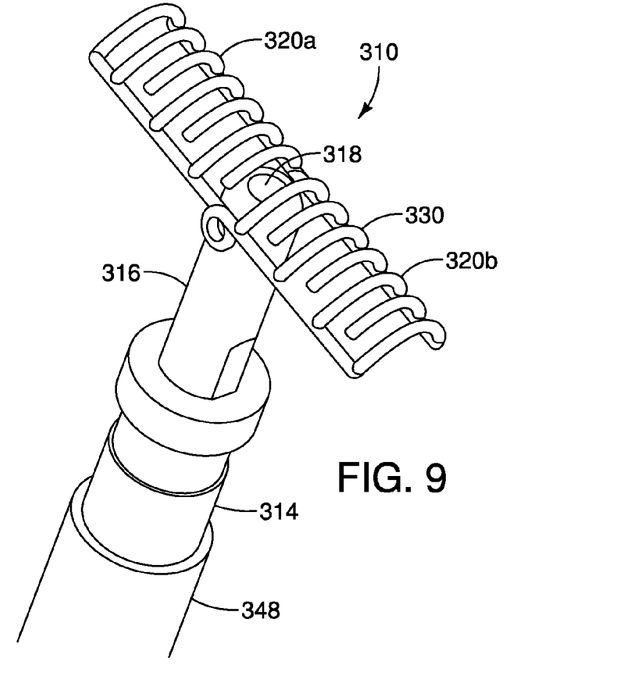
FIG. 9 is a perspective view of an embodiment of an expandable probe in accordance with the present invention.

As shown in FIG. 9, an embodiment of an expandable probe 310 includes a pair of arms 320a, 320b that also are the electrodes 330. The arms 320a, 320b are movable similar to the arms 20 described above. The electrodes 330 forming each arm 320a, 320b may be separately energized as described above. A flush port 318 may be provided at the distal portion 316 that is fluidly connected to a shaft 314. An outer sheath 348 may be provided that fits over the arms 320a, 320b for delivery to the treatment site and then is proximally withdrawn to expose the arms 320a, 320b. In some embodiments, a hinge member may also be provided.

The material of the arms 320a, 320b may be a shape memory alloy that expands once the arms have been advanced from the endoscope to the treatment site and the alloy is warmed so that the arms 320a, 320b expand to the expanded confirmation 24 as shown in FIG. 9. The shape memory alloy may be cooled, for example, by flushing chilled solution through the flush port 318 to return the arms 320a, 320b to the closed configuration 22 (see FIG. 1, for example). Other electroconductive materials may also be used to form the arms 320a, 320b.

Figures 10, 11:
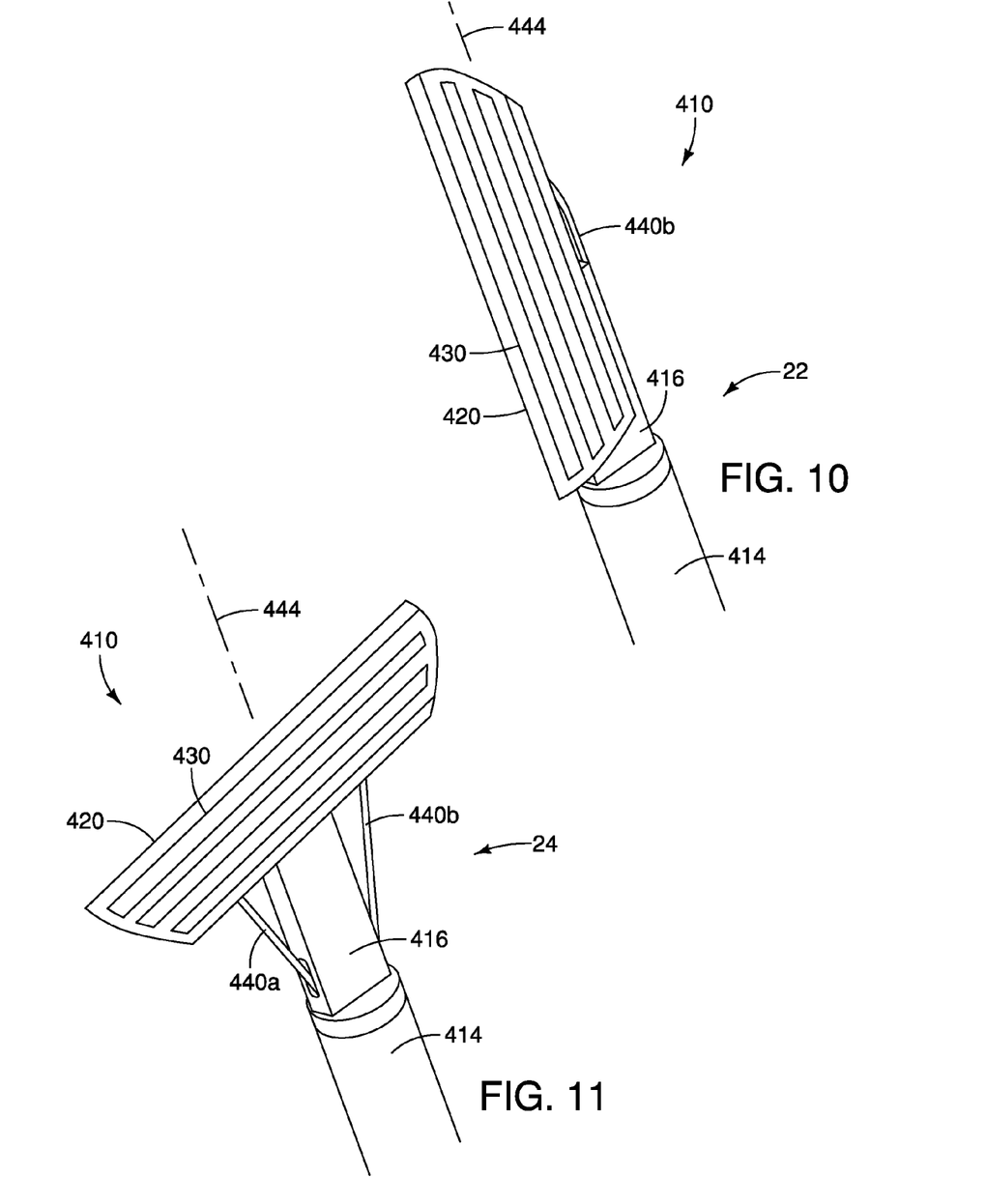
FIG. 10 is a side view of an embodiment of an expandable probe in accordance with the present invention.
FIG. 11 is a side view of the embodiment shown in FIG. 10 in the expanded configuration.
Figure 12:
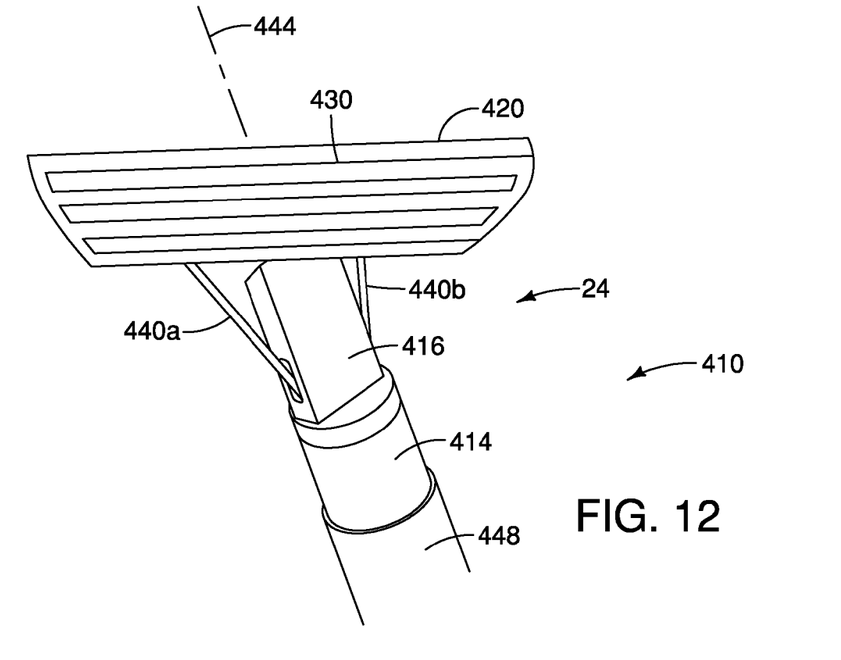
FIG. 12 is a side view of the embodiment shown in FIG. 10.
Figure 13:
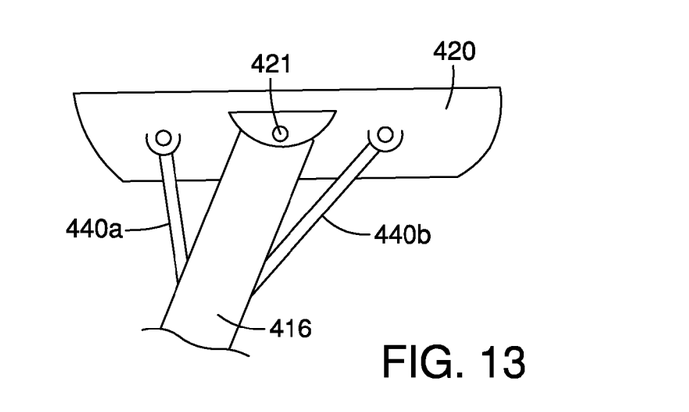
FIG. 13 is a sectional view of a portion of the embodiment shown in FIG. 10.

FIGS. 10-13 illustrate an embodiment of an expandable probe 410 having a single arm 420 that is movable between the closed configuration 22 and the expanded configuration 24. The closed configuration 22 is shown in FIG. 10 where the arm 420 extends substantially parallel to a longitudinal axis 444. Similar to the embodiments described above, the arm 420 may include 1 or more electrodes 430 in any pattern on the arm 420. The electrodes 430 bipolar or monopolar and may be energized in sections on the arm 420. FIGS. 11 and 12 illustrate the expandable probe 410 in the expanded configuration 24 where the arm 420 is extended away from the longitudinal axis 444. One or more wires 440 may be used to move the arm 420 between the closed configuration 22 and the expanded configuration 24. As shown in FIGS. 11 and 12, a pair of wires 440a, 440b may cooperate to position the arm 420 for treatment of the tissue. As shown in FIG. 13, the arm 420 may pivot on a pivot 421. The wires 440a, 440b may be connected to portions of the arm 420 and one wire 440a or 440b may be moved to position the arm 420 or both wires, 440a, 440b may be moved to position the arm 420, for example by pulling wire 440b proximally and pushing the arm 440a distally, the arm 420 may be positioned as shown in FIG. 12. In some embodiments, one wire 440 may be used to pivot the arm 420 on the pivot 421. An outer sheath 448 may be provided to hold the arm 420 in the closed configuration 22 for delivery to the treatment site.

Figure 14:
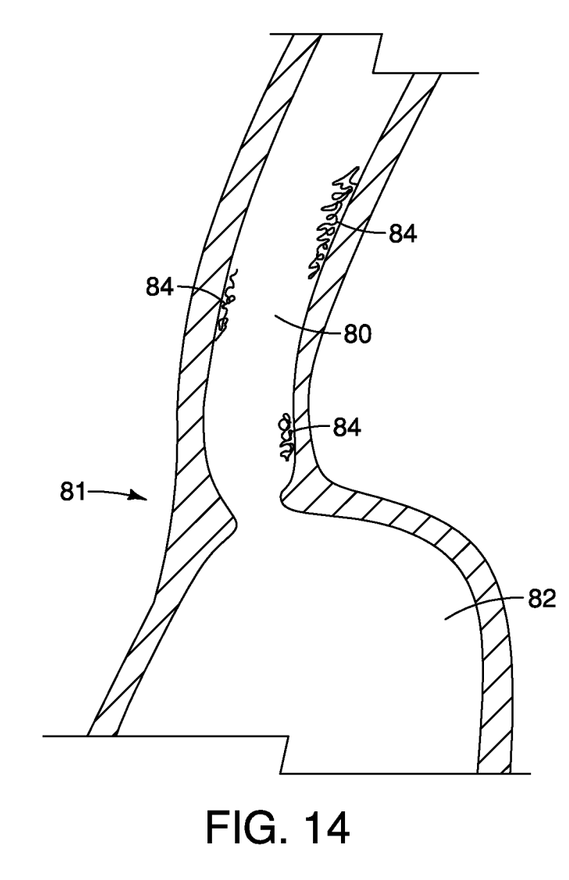
FIGS. 14-16 illustrate operation of the expandable probe.
Figure 15:
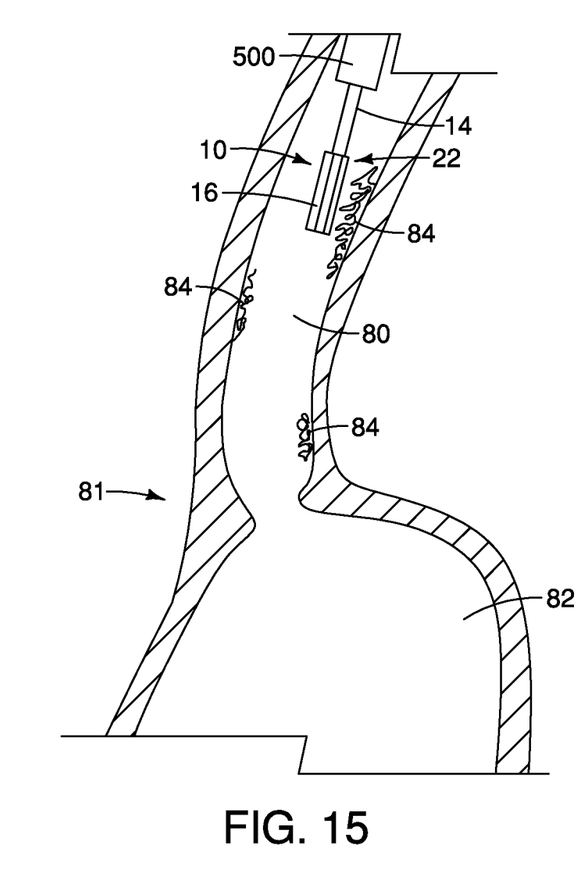
Figure 16:
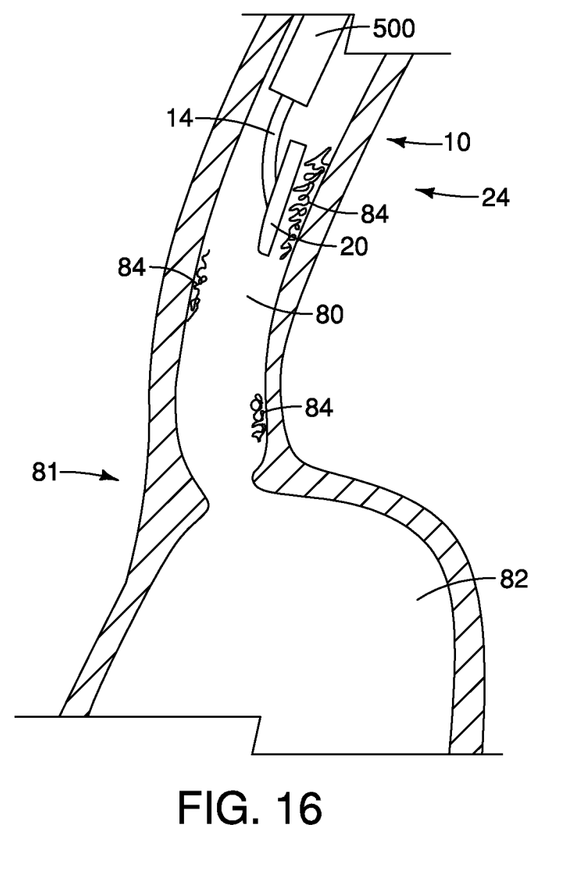

Operation of the expandable probe will be explained with reference to the expandable probe 10 as an example. Operation of the expandable probe 10 is shown in FIGS. 14-16. FIG. 14 illustrates a patient's esophagus 80, lower esophageal sphincter (LES) 81 and stomach 82. Areas of diseased tissue 84 within the esophagus 80 are also shown. The diseased tissue 84 may be columnar mucosa (Barrett's esophagus) that is to be ablated using the expandable probe 10. FIG. 15 illustrates the distal portion 16 of the expandable probe 10 extending from an optional endoscope 500. The expandable probe 10 is in the closed configuration 22 in the patient's esophagus 80. The expandable probe 10 is positioned in the esophagus 80 near the portion of the diseased tissue 84 to be treated. The insertion of the expandable probe 10 may be monitored using the viewing port of the endoscope 500 to help position the expandable probe 10 at the diseased tissue. The expandable probe 10 may be energized in the closed configuration 22 and/or the open configuration 24 depending on the size of the area of tissue to be treated. By way of non-limiting example, for the arm 20 having an electrode area of about 0.2 inches×0.05 inches, an area of about 0.02 inches$^2$ may be the area ablated in the closed configuration 22. For a pair of arms 20 having the same size electrode area, an area of about 0.02 inches$^2$ may be treated in the expanded configuration 24.

The expanded configuration 24 is shown in FIG. 15, where the arms 20a, 20b are expanded away from the shaft 14 and pressed against the diseased tissue 84. The diseased tissue has been brought into contact with the electrodes 30 or an electroconductive fluid flushed through the flush port 18. The power source 60 is activated for a sufficient time to ablate the diseased tissue 84. If the expandable probe 10 is in the expanded configuration 24, the arms 20a, 20b may be folded into the closed configuration 22 and moved to another location and the steps repeated as many times as needed. While the procedure has been described with reference to the ablation of diseased tissue in the esophagus using the expandable probe 10, the location of the treatment is not limited to the esophagus. By way of non-limiting example, portions of the stomach, or the gastrointestinal tract may also be treated using the expandable probe 10.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An expandable probe comprising:
    an elongate shaft having a proximal portion, a distal portion, a lumen extending at least partially therethrough and a longitudinal axis; and
    an arm operably connected to the distal portion, the arm having a first surface comprising an electrode extending over at least a portion of the first surface; the electrode being operably connectable to an energy source;
    wherein the arm comprises a closed configuration and an expanded configuration, the arm in the closed configuration extends substantially parallel to the longitudinal axis and in the expanded configuration the arm extends away from the longitudinal axis, the electrode is energizable in the closed configuration and the expanded configuration of the arm.

2. The expandable probe of claim 1, wherein the arm extends at about 90° from the longitudinal axis.

3. The expandable probe of claim 1, wherein the arm extends less than about 90° from the longitudinal axis.

4. The expandable probe of claim 1, further comprising a pair of arms, each arm comprising at least one electrode.

5. The expandable probe of claim 4, wherein the arms are independently extendable away from the longitudinal axis.

6. The expandable probe of claim 5, wherein one arm is in the expanded configuration and one arm is in the closed configuration for delivery of energy to the tissue source.

7. The expandable probe of claim 1, further comprising a control wire operably connected to the arm for moving the arm to the expanded and closed configurations.

8. The expandable probe of claim 1, wherein the arm comprises a second surface comprising an electrode extending over at least a portion of the second surface.

9. The expandable probe of claim 1, further comprising a hinge member operably connected to the shaft and to the arm.

10. The expandable probe of claim 1, further comprising a flush port operably connected to the lumen.

11. The expandable probe of claim 1, wherein the electrode comprises bipolar electrodes.

12. The expandable probe of claim 1, wherein the arm comprises a transparent material or a translucent material.

13. The expandable probe of claim 1, wherein the arm comprises an energy transmitting material.

14. The expandable probe of claim 1, further comprising an energy source wherein the energy source comprises RF energy.

15. The ablation probe of claim 1, further comprising an endoscope, the ablation probe being deliverable through a working channel of the endoscope to the tissue site.

16. A method of delivering energy to a tissue site within a patient's lumen, the method comprising:
    positioning an ablation probe within a patient's lumen, the ablation probe comprising:
        an elongate shaft having a proximal portion, a distal portion, a lumen extending at least partially therethrough and a longitudinal axis; and
        an arm operably connected to the distal portion, the arm having a first surface comprising an electrode extending over at least a portion of the first surface; the electrode being operably connectable to an energy source and energizable in an expanded configuration and in a closed configuration of the arm;
    supplying energy to the electrode; and
    ablating the tissue with the arm in the expanded configuration or the closed configuration.

17. The method of claim 16, further comprising expanding the arm away from the longitudinal axis to the expanded configuration.

18. The method of claim 17, further comprising moving the arm to the closed configuration and repositioning the expandable probe at a second tissue site to be treated.

19. The method of claim 18, further comprising expanding the arm away from the longitudinal axis to the expanded configuration.

20. The method of claim 16, further comprising flushing the tissue through a flush port on the ablation probe.

* * * * *